United States Patent
Lo et al.

(12) 
(10) Patent No.: US 6,321,607 B1
(45) Date of Patent: Nov. 27, 2001

(54) COLLECTING APPARATUS FOR AUTOMATICALLY COLLECTING SAMPLE DURING PARTICULAR TIME INTERVAL

(76) Inventors: Jium Guang Lo; Shun Shiang Keh; Jiun Yi Yang, all of No. 101, Sec. 2, Kwangfu Rd., Hsinchu (TW)

( * ) Notice: Subject to any disclaimer, the term of this patent is extended or adjusted under 35 U.S.C. 154(b) by 0 days.

(21) Appl. No.: 09/261,066

(22) Filed: Mar. 2, 1999

(30) Foreign Application Priority Data

Oct. 1, 1998 (TW) .......................................... 87116375 A

(51) Int. Cl.$^7$ ...................................................... G01N 1/00
(52) U.S. Cl. .......................................................... 73/863.11
(58) Field of Search ........................... 73/863.01, 863.11, 73/863.31, 863.33, 864.34

(56) References Cited

U.S. PATENT DOCUMENTS

| | | | |
|---|---|---|---|
| 3,921,456 | * 11/1975 | Newcomb et al. | 73/863.31 |
| 4,454,772 | * 6/1984 | Brunner et al. | 73/863.33 |
| 4,704,910 | * 11/1987 | Conrad | 73/863.31 |
| 4,886,966 | * 12/1989 | Matsunaga et al. | |
| 5,167,802 | * 12/1992 | Sandstrom et al. | 73/864.34 |
| 5,469,751 | * 11/1995 | Weiss et al. | 73/863.33 |

* cited by examiner

*Primary Examiner*—Robert Raevis
(74) *Attorney, Agent, or Firm*—Klein & Szekeres LLP

(57) ABSTRACT

A collecting apparatus for automatically collecting a sample during a particular time interval is disclosed. The collecting apparatus includes a power supply for providing an electric power to operate the collecting apparatus and a plurality of sampling units. Each sampling unit includes a timing device for counting down and generating a first starting signal at a specific time for collecting the sample, a valve for allowing the sample to enter the sampling unit, a valve controller electrically connected to the timing device for generating a timing signal to open/close the valve after receiving the first starting signal, and a collector connected with the valve for collecting the sample through the valve. The collector includes a tube connecting to the valve, a reservoir connected to one end of the tube for containing the sample, and a flow controller connected to the other end of the tube for controlling the flow rate of the sample entering the reservoir. The pressure in the reservoir is less than $10^{-2}$ torr so that the sample spontaneously enters the reservoir. The electric power can be an alternating current with 110 V or a direct current with 24 V. By using this collecting apparatus, 12 different samples can be automatically collected at different times.

10 Claims, 2 Drawing Sheets

COLLECTING APPARATUS FOR AUTOMATICALLY COLLECTING SAMPLE DURING PARTICULAR TIME INTERVAL

FIELD OF THE INVENTION

The present invention relates to a collecting apparatus, more particularly to a collecting apparatus for automatically collecting a sample during a particular time interval.

BACKGROUND OF THE INVENTION

In a conventional method for collecting a gaseous sample, the worker needs to collect a lot of samples at different sampling spots and different sampling time. These sampling spots and sampling time depend on the conditions of this experimental area. These conditions include the direction of wind, the position of the polluting area, and the experimental environment, etc. The sampling times may be any time in a whole day and then the worker must collect several samples in a sampling spot during 24 hours regardless of day or night. If the experimental area is very big, the number of the sampling spots will be increased and the frequency of sampling will be also increased. So, the worker must make much effort in this job. Therefore, it is tried by the applicant to deal with this problem encountered with the prior art.

SUMMARY OF THE INVENTION

An object of the present invention is to provide a collecting apparatus for automatically collecting a sample during a particular time interval.

The collecting apparatus for automatically collecting a sample includes a power supply for providing an electric power to operate the collecting apparatus and a plurality of sampling units. Each sampling unit includes a timing device for counting down and generating a first starting signal at a specific time for collecting the sample, a valve for allowing the sample to enter the sampling unit, a valve controller electrically connected to the timing device for generating a timing signal to open/close the valve after receiving the first starting signal, and a collector connected with the valve for collecting the sample through the valve.

In accordance with an aspect of the present invention, the apparatus includes 12 sampling units.

In accordance with another aspect of the present invention, the timing device is an electronic timer.

In accordance with another aspect of the present invention, the timing signal includes a second starting signal and an ending signal to define therebetween the particular time interval for causing the valve controller to open and close the valve respectively.

In accordance with another aspect of the present invention, the signals are electrical impulses.

In accordance with another aspect of the present invention, the valve controller is an electronic controller.

In accordance with another aspect of the present invention, the particular time interval is ranged from ten seconds to six hours.

In accordance with another aspect of the present invention, the collector includes a tube connecting to the valve, a reservoir connected to one end of the tube for containing the sample, and a flow controller connected to the other end of the tube for controlling the flow rate of the sample entering the reservoir.

In accordance with another aspect of the present invention, the sample is a volatile organic gas.

In accordance with another aspect of the present invention, the tube is a U-shaped tube.

In accordance with another aspect of the present invention, the tube is a chemical inert stainless tube.

In accordance with another aspect of the present invention, there is a heater mounted around the tube for heating the tube when collecting the sample to prevent the organic gas from being adsorbed in the tube.

In accordance with another aspect of the present invention, the pressure in the reservoir is less than $10^{-2}$ torr so that the sample spontaneously enters the reservoir.

In accordance with another aspect of the present invention, the reservoir is made of stainless steel.

In accordance with another aspect of the present invention, the stainless steel reservoir has an electroplating coating on an inner surface of the reservoir for preventing the surface from being contaminated by the sample.

In accordance with another aspect of the present invention, the electric power provided by the power supply is a direct current of 24 V.

In accordance with another aspect of the present invention, the direct current is converted from an alternating current of 110 V provided by a utility power.

In accordance with another aspect of the present invention, the direct current is provided by a battery.

In accordance with another aspect of the present invention, the battery is a rechargeable battery.

The present invention may best be understood through the following description with reference to the accompanying drawings, in which:

DETAILED DESCRIPTION OF THE PREFERRED EMBODIMENTS

Figure 1:
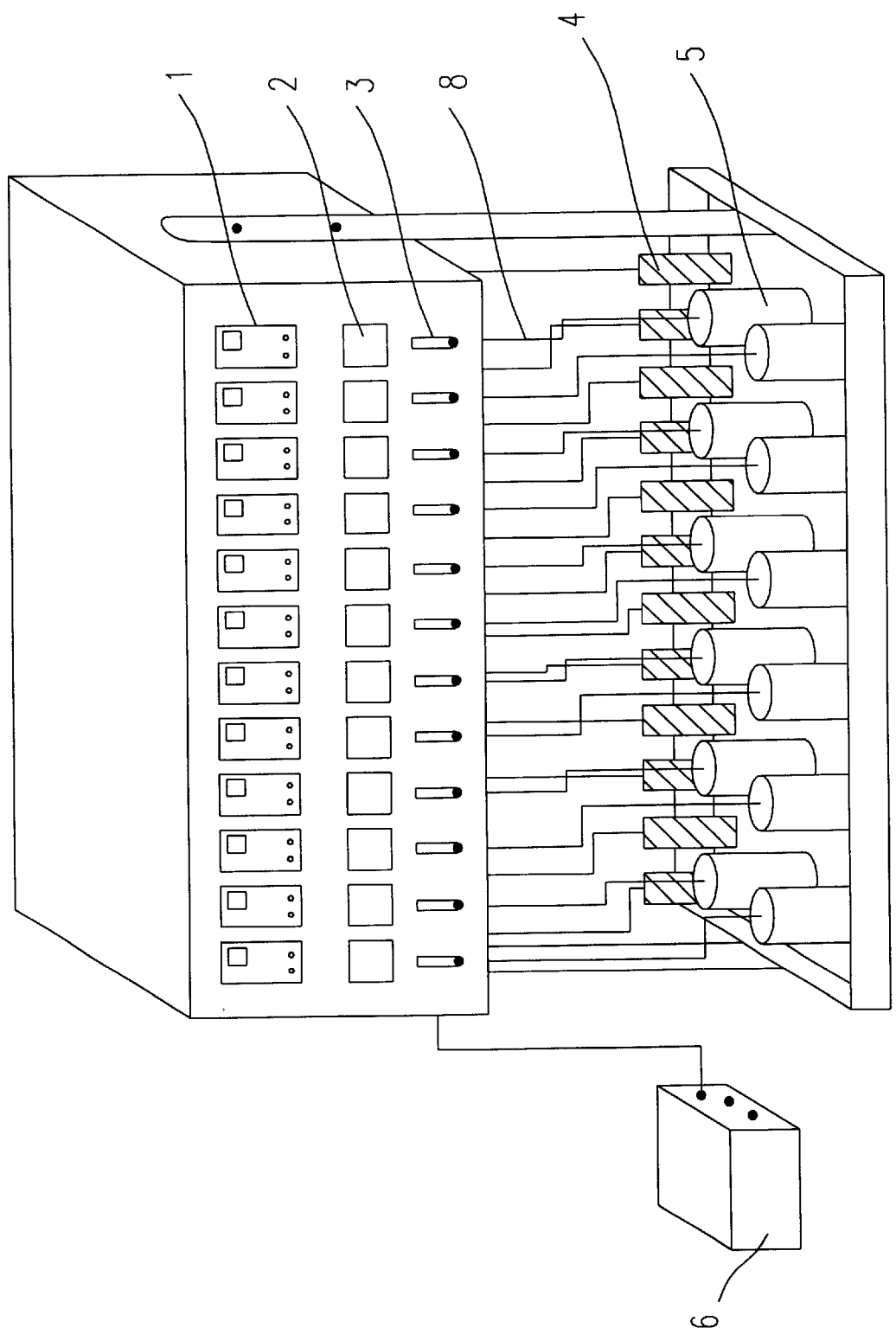
FIG. 1 is a schematic diagram showing a preferred embodiment of the collecting apparatus according to the present invention.

Referring to FIG. 1, the collecting apparatus for automatically collecting a sample during a particular time interval disclosed in the present invention includes a power supply 6 and 12 sampling units. The power supply is used for providing an electric power of 110 V to operate the collecting apparatus. Each sampling unit includes a timing device 1, a valve controller 2, a valve 3, a flow controller 4, a reservoir 5, and a tube 8. The worker does not need to arrive at the collecting spot at the actual sampling time. First, the worker can put one collecting apparatus at the collecting spot and set a timing interval representing the difference between the actual time and the sampling time. For example, the worker arrives at the collecting spot at 8:00 am and wants to collect a sample at 11:00 am, then, he needs to set a 3-hour interval. The timing device 1 is an electronic timer which can count down the time and output a first starting signal when the time is up. The first starting signal is transmitted to the valve controller 2 and the valve controller 2 will output a second signal for opening the valve 3 to allow the sample to enter the sampling unit. The sample passes through the tube 8 and stores in the reservoir 5. Finally, the valve controller 2 outputs an ending signal to close the valve 3. The second starting signal and the ending signal are used to define a particular time interval for collecting the sample.

The particular time interval of the second first signal and the ending signal are ranged from ten seconds to six hours. That is, the valve 3 opens for ten seconds when the worker set a specific time to start the collecting process. If the worker wants to collect the sample during a time interval, two hours for example, the opening time of the valve 3 is 2 hours rather than ten seconds. The opening time of the valve 3 is up to six hours if necessary. The sample is a volatile organic gas, and the flow rate of the sample can be adjusted by the flow controller 4.

When the collecting apparatus is placed outdoors, the electric power provided by the power supply is a direct current of 24 V. The direct current can be converted from an alternating current of 110 V or provided by a rechargeable battery.

Figure 2:
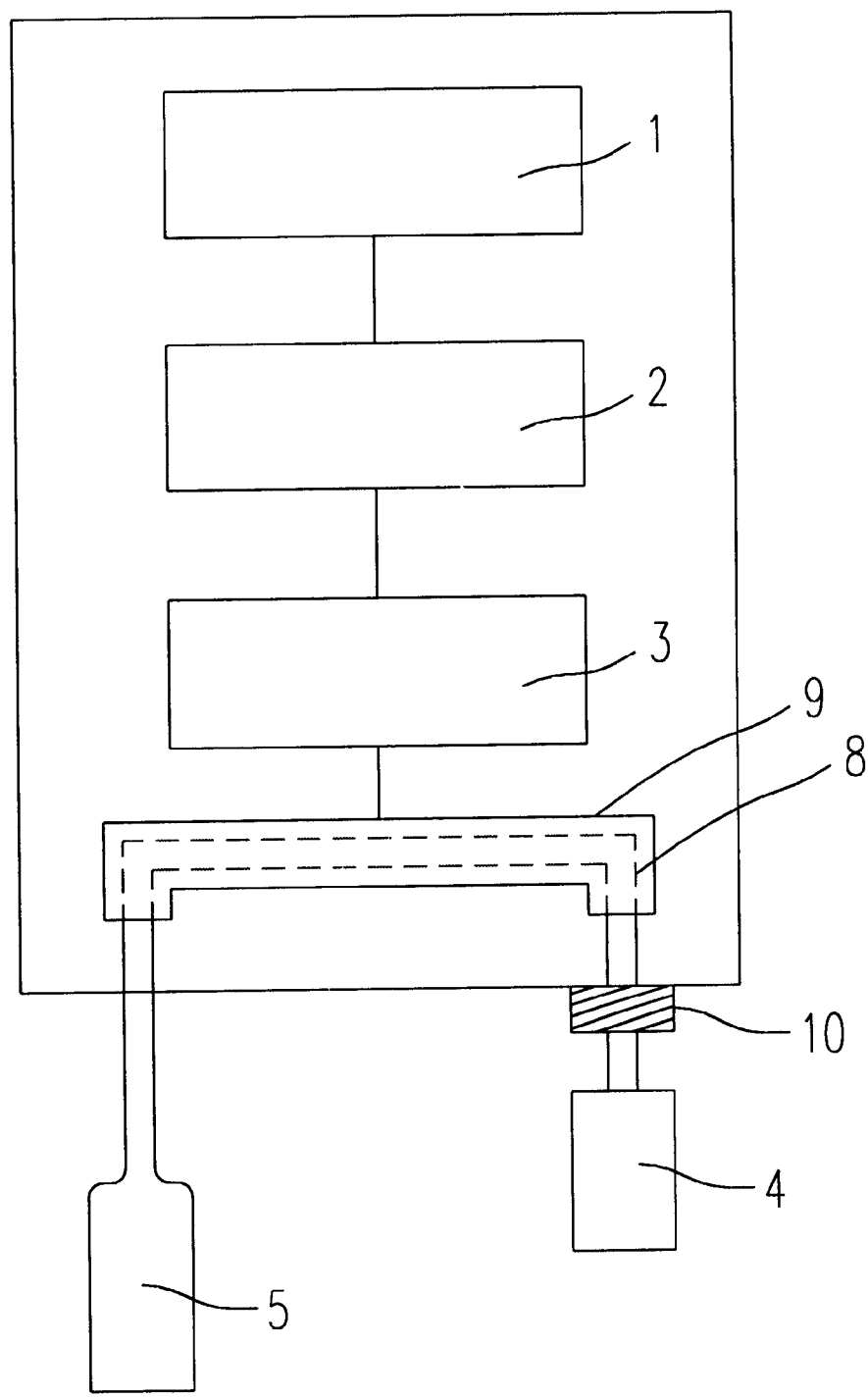
FIG. 2 is a detailed diagram showing the preferred embodiment of the collecting apparatus with a sampling unit according to the present invention.

Referring to the FIG. 2, the tube 8 is a U-shaped chemically inert stainless tube. When the sample enters the tube 8 from the entrance 10, the tube is heated by the heater 9 to prevent the organic gas from being adsorbed in the tube.

The pressure in the reservoir 5 is less than $10^{-2}$ torr so that the sample spontaneously enters the reservoir. The reservoir 5 is made of stainless steel and has an electroplating coating on an inner surface of the reservoir for preventing the surface from being contaminated by the sample.

If the worker needs to collect two or more samples in different time intervals, the number of sampling units can be greater than one. The operation of the collecting apparatus with one sampling unit is similar to that with a plurality of sampling units. Preferably, the worker can collect 12 samples by using the collecting apparatus at one place. The volume of the reservoir 5 can be two or six liters according to the amount of the sample. The volume of the reservoir 5 can be also expanded. The number of the sampling unit and the volume of the reservoir 5 depend on the need of the experiment.

It is very easy and convenient to use the collecting apparatus for automatically collecting samples. By using this collecting apparatus, 12 different samples can be automatically collected at different times. Therefore, it can save a lot of money and time for a worker to collect these samples respectively.

While the invention has been described in terms of what are presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A collecting apparatus for automatically collecting a sample during a particular time interval comprising:
   a power supply for providing an electric power to operate said collecting apparatus; and
   at least one individually operating sampling unit electrically connected to said power supply, said sampling unit comprising:
      a timing device for counting down and generating a starting signal at a specific time for collecting said sample;
      a valve for allowing said sample to enter said sampling unit;
      a valve controller electrically connected to said timing device for generating an opening signal and an ending signal to open and close said valve respectively after receiving said starting signal; and
      a collector connected with said valve for collecting said sample through said valve,
   wherein said collector further comprises:
      a tube connected to said valve;
      a heater mounted around said tube for heating said tube when collecting said sample to prevent said sample from being adsorbed in said tube;
      a reservoir connected to one end of said tube for containing said sample, wherein said reservoir is made of stainless steel and has an electroplating coating on an inner surface of said reservoir for preventing said inner surface from being contaminated by said sample; and
      a flow controller connected to the other end of said tube for controlling the flow rate of said sample entering said reservoir.

2. The apparatus according to claim 1 wherein said particular time interval is defined as a time interval between a time point of opening and a time point of closing said valve.

3. The apparatus according to claim 1 wherein said particular time interval is ranged from ten seconds to six hours.

4. The apparatus according to claim 1 wherein said sample is a volatile organic gas.

5. The apparatus according to claim 1 wherein said tube is a U-shaped tube.

6. The apparatus according to claim 1 wherein a pressure in said reservoir is less than $10^{-2}$ torr so that said sample spontaneously enters said reservoir.

7. The apparatus according to claim 1 wherein said electric power provided by said power supply is a direct current of 24 V.

8. The apparatus according to claim 7 wherein said direct current is converted from an alternating current of 110 V provided by a utility power.

9. The apparatus according to claim 8 wherein said direct current is provided by a battery.

10. The apparatus according to claim 9 wherein said battery is a rechargeable battery.

* * * * *